United States Patent [19]

Uhle et al.

[11] 4,369,649
[45] Jan. 25, 1983

[54] TESTING METHOD FOR DETERMINING THE MAGNETIC PROPERTIES OF FERROMAGNETIC POWDERS

[75] Inventors: Karlheinz Uhle, Brühl; Horst Krämer, Hürth-Hermülheim, both of Fed. Rep. of Germany

[73] Assignee: Hoechst Aktiengesellschaft, Fed. Rep. of Germany

[21] Appl. No.: 261,769

[22] Filed: May 8, 1981

[30] Foreign Application Priority Data

May 16, 1980 [DE] Fed. Rep. of Germany ....... 3018639

[51] Int. Cl.$^3$ ............................................. G01N 15/04
[52] U.S. Cl. ........................................ 73/61.4; 209/8; 356/442
[58] Field of Search ............... 73/61.4; 356/441, 442; 209/8, 39

[56] References Cited

FOREIGN PATENT DOCUMENTS 488118 1/1976 U.S.S.R. ............................... 73/61.4
623140 9/1978 U.S.S.R. ............................... 73/61.4

*Primary Examiner*—Edward R. Kazenske
*Assistant Examiner*—Joseph W. Roskos
*Attorney, Agent, or Firm*—Connolly and Hutz

[57] ABSTRACT

The invention relates to a method permitting ferromagnetic powders for use in heavy medium suspensions for the float-sink dressing of minerals to be readily tested as to their efficiency in magnetic separation and demagnetization. To this end, the invention provides (a) for a heavy medium suspension specimen to be removed from the purification cycle directly downstream of the magnetic separation stage, for it to be freed from impurities by decantation, and its relative sedimentation velocity to be determined with the aid of a sedimentometer;

(b) for a heavy medium suspension specimen to be removed from the purification cycle downstream of the demagnetization stage, for it to be freed from impurities by decantation, and for its relative sedimentation velocity to be determined with the aid of a sedimentometer; and (c) for the heavy medium suspension specimen according to (b) to be demagnetized in a cyclicly decreasing magnetic alternating field with a maximum field strength which is 1.1 to 1.5 times the maximum field strength of the magnetic separator, and for the relative sedimentation velocity of the specimen to be determined with the aid of sedimentometer. The ferromagnetic powder is reliably separable magnetically and demagnetizable with the aid of a demagnetizing means in the event of the relative sedimentation velocity according to (a) being at least ten times greater than the relative sedimentation velocity according to (c), and the relative sedimentation velocity according to (c) being at most 10% lower than that according to (b).

2 Claims, 1 Drawing Figure

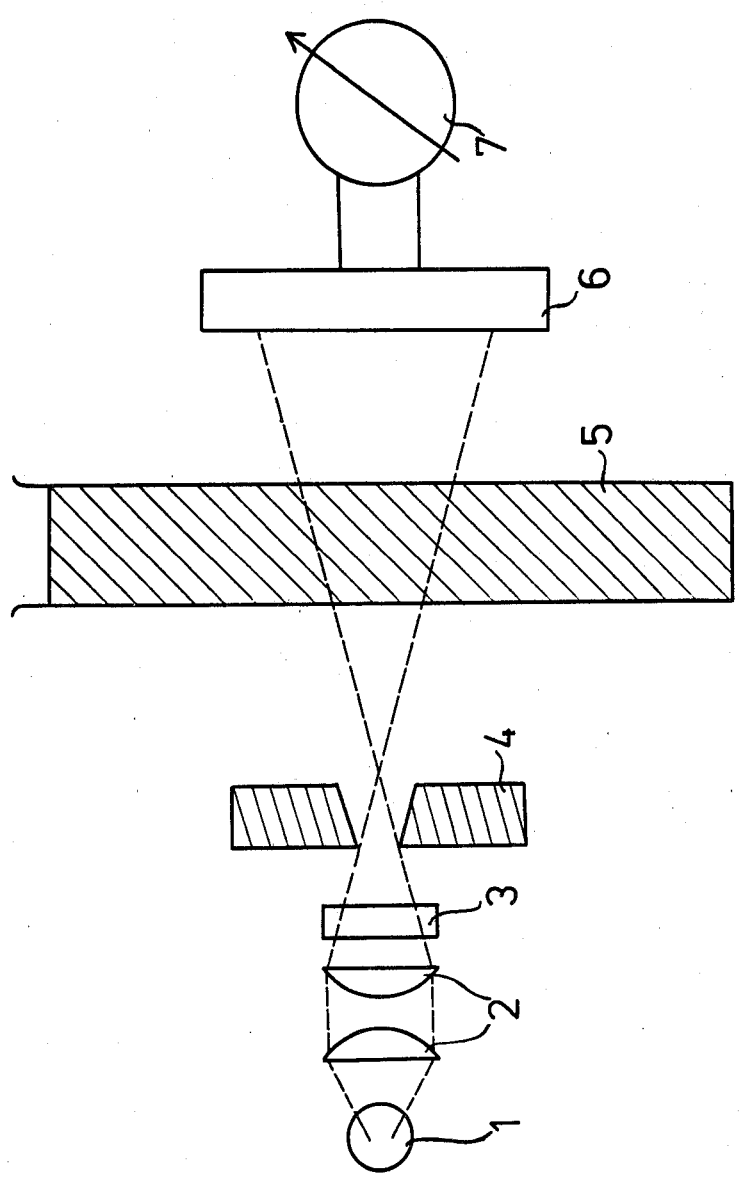

TESTING METHOD FOR DETERMINING THE MAGNETIC PROPERTIES OF FERROMAGNETIC POWDERS

The present invention provides a method permitting ferromagnetic powders which are used in heavy medium suspensions for the float-sink dressing of minerals, to be tested as to their efficiency in magnetic separation and demagnetization.

Float-sink dressing is a process which is customarily used for separating minerals of different density from each other with the use of an aqueous suspension of a heavy medium, i.e. with the use of a so-called heavy medium suspension with a specific density which lies between the densities of the respective minerals which are to be separated from each other. As a result, upon the introduction of the mixture of minerals into the heavy medium suspension, it is possible for mixture constituents of lower density to float thereon, and for mixture constituents of higher density to sink down and settle therein. Needless to say, portions of the heavy medium suspension adhere to the floating and settled materials. For recovery, the materials are separated from one another and subjected to treatment with a water jet, the adhering heavy medium being then obtained in the form of a dilute suspension. The small particle size makes it impossible for the heavy medium to be separated, e.g. by filtration from such dilute suspension. This is the reason why ferromagnetic powders are preferentially used as heavy media as these can be recovered from a dilute suspension by magnetic separation and can additionally be freed from unmagnetic contaminants. Magnetite has more particularly been used for making heavy medium suspensions of relatively low specific density, and ferrosilicon with 8 to 25% Si therein has been used for making heavy medium suspensions of higher specific density, the heavy medium, which is incidentally made by a spray or grinding process, being employed in the form of particles with a size within the range about 0.001 to 0.4 mm. Magnetically separated heavy medium is invariably magnetized, i.e. constitutes powder which is unable to produce a stable suspension. In other words, any heavy medium which is so recovered has to be demagnetized for re-use in the preparation of fresh heavy medium suspensions. It has been described that any recovered heavy medium can be demagnetized by demagnetization in an alternating field (cf. "Stahl und Eisen", 74 (1954), pages 1070 to 1075). Depending on the production facility, quality and quantity of the feed materials, it is possible to produce pulverulent heavy media with more or less good magnetic properties, which naturally influence their demagnetizability in the alternating field. Especially in those cases in which the heavy medium (e.g. ferrosilicon) has further corrosion-improving materials, e.g. carbon together with phosphorus, copper, aluminium or similar materials, admixed with it (cf. German Patent Specifications Nos. 972 687 and 2,222,657), the resulting multimaterial system cannot be said to have well-defined magnetic properties.

It is therefore the object of the present invention to provide a method permitting ferromagnetic powders for use in heavy medium suspensions for the float-sink dressing of minerals to be readily tested as to their efficiency in magnetic separation and demagnetization, which comprises:

(a) removing a heavy medium suspension specimen from the purification cycle directly downstream of the magnetic separation stage, freeing the specimen from impurities by decantation, and determining its relative sedimentation velocity with the aid of a sedimentometer;

(b) removing a heavy medium suspension specimen from the purification cycle downstream of the demagnetization stage, freeing the specimen from impurities by decantation, and determining its relative sedimentation velocity with the aid of a sedimentometer; and (c) demagnetizing the heavy medium suspension specimen according to (b) in a cyclicly decreasing magnetic alternating field with a maximum field strength which is 1.1 to 1.5 times the maximum field strength of the magnetic separator, and determining the relative sedimentation velocity of the specimen with the aid of a sedimentometer, the ferromagnetic powder being reliably separable magnetically and demagnetizable with the aid of a demagnetizing means in the event of the relative sedimentation velocity according to (a) being at least ten times greater than the relative sedimentation velocity according to (c), and the relative sedimentation velocity according to (c) being at most 10% lower than that according to (b).

The maximum field strength of the alternating field is preferably 1.4 times the maximum field strength of the magnetic separator.

Use is made of quantitatively small specimens in the testing method of this invention which permits ferromagnetic powder for use in heavy medium suspensions to be rapidly tested as to whether, on the one hand, it is magnetizable enough to ensure reliable magnetic separation from an aqueous phase and as to whether, on the other hand, it is magnetically soft enough to ensure satisfactory demagnetization.

The sedimentometer used in the testing method of this invention is shown diagrammatically in the accompanying drawing.

With reference thereto:

A collector system 2 formed of a plurality of lenses is exposed to the light of a low-voltage lamp, which is used as a light source 1. The light ray coming from the collector system 2 is passed through a heat-absorbing filter 3 and a slit-shaped shutter 4 and directed to impinge upon a glass cylinder 5 having heavy medium suspension placed in it. The light ray portion penetrating through the glass cylinder 5 impinges upon a photoelectric cell 6 which is electrically connected to a measuring instrument 7.

Depending on the sedimentation velocity determined for the powder in the heavy medium suspension, the measuring instrument 7 commences deflecting when the last powder particles which are largest in diameter have dropped past it.

The sedimentation velocity is determined in accordance with the testing method of this invention on the evidence of the spacing between the slit-shaped shutter 4 and the level of heavy medium suspension in the glass cylinder 5 and the period which elapses from the insertion, into the sedimentometer, of the glass cylinder 5 just filled with freshly agitated or shaken heavy medium suspension, until response of the measuring instrument 7 by a defined deflection. The defined deflection is 10% of that which is produced by the measuring instrument in the event of the glass cylinder 5 being filled with water free from solid matter.

EXAMPLE 1

A specimen of heavy medium suspension was taken from the heavy medium (ferrosilicon which contained 12.5% silicon and 1% phosphorus) purification cycle directly downstream of the magnetic separation stage, freed from impurities by decantation and shaken. Next, a specimen portion was filled 16 cm high into a test tube which was 18 cm long and had an inner diameter of 18 cm. Prior to inserting the test tube in a sedimentometer, the specimen was shaken once again. 3 seconds after insertion, the measuring instrument of the sedimentometer indicated a photo-electric current of 0.3 $\mu$A. Calculation based on this value and the spacing between level of heavy medium suspension and slit-shaped shutter indicated a relative sedimentation velocity of 2.7 cm/second.

In the manner described there was also determined and calculated the relative sedimentation velocity of a heavy medium suspension specimen taken from the heavy medium purification cycle downstream of the demagnetization stage, which was 0.067 cm/second. Next, the specimen was demagnetized in an alternating field with a maximum field strength which was 1.4 times that of the magnetic separator. The relative sedimentation velocity of the demagnetized specimen was found to be 0.065.

EXAMPLES 2 TO 4

The procedure of Example 1 was repeated but the charging rate for the demagnetizing coil in the demagnetization cycle was varied.

The results obtained in Examples 1 to 4 are indicated in the following Table. Index of the charging rate selected for the demagnetizing coil is the deflection of its ammeter in arbitrary scale division, higher scale values indicating higher charging rates. With further reference to the Table:

Column I relates to a heavy medium suspension specimen taken directly downstream of the magnetic separation stage;

Column II relates to a heavy medium suspension specimen taken downstream of the demagnetization coil, and:

Column III relates to specimen of II demagnetized in an alternating field, of which the maximum field strength is 1.4 times the maximum field strength of the magnetic separator.

| Ex. No. | Charging rate Demagnetization coil (Scale division) | Relative sedimentation velocity I | II | III |
|---|---|---|---|---|
| 1 | 3 | 2.7 | 0.067 | 0.065 |
| 2 | 4 | 2.6 | 0.065 | 0.065 |
| 3 | 2 | 2.6 | 0.071 | 0.065 |
| 4 | 1 | 2.6 | 0.285 | 0.064 |

In the case of the heavy medium suspensions used in Examples 1 to 3, the I-specimens underwent sedimentation more than 10 times more rapidly than the II-specimens, and the relative sedimentation velocities of the II- and III-specimens were found to differ from one another by less than 10%.

Under the conditions selected for the charging rate of the demagnetization coil, the ferrosilicon-based heavy medium suspension in the purification cycle was found to be reliably separable magnetically and demagnetizable.

In the case of the heavy medium suspension used in Example 4, the I-specimen underwent sedimentation only nine times more rapidly than the II-specimen, and the relative sedimentation velocities of II and III were found to differ from one another by considerably more than 10%. Under these conditions which were selected for the charging rate of the demagnetization coil, it was no longer possible for the heavy medium suspension to be satisfactorily demagnetized.

We claim:

1. A method permitting ferromagnetic powders for use in heavy medium suspensions for the float sink dressing of minerals to be tested as to their efficiency in magnetic separation and demagnetization, which comprises:
   (a) removing a heavy medium suspension specimen from the purification cycle directly downstream of the magnetic separation stage, freeing the specimen from impurities by decantation, and determining the relative sedimentation velocity with the aid of a sedimentometer;
   (b) removing a heavy medium suspension specimen from the purification cycle downstream of the demagnetization stage, freeing the specimen from impurities by decantation, and determining its relative sedimentation velocity with the aid of a sedimentometer; and
   (c) demagnetizing the heavy medium suspension specimen according to (b) in a cyclicly decreasing magnetic alternating field with a maximum field strength which is 1.1 to 1.5 times the maximum field strength of the magnetic separator, and determining the relative sedimentation velocity of the specimen with the aid of a sedimentometer,
the ferromagnetic powder being reliably separable magnetically and demagnetizable with the aid of a demagnetizing means in the event of the relative sedimentation velocity according to (a) being at least ten times greater than the relative sedimentation velocity according to (b), and the relative sedimentation velocity according to (c) being at most 10% lower than that according to (b).

2. The testing method as claimed in claim 1, wherein the maximum field strength of the alternating field is 1.4 times the maximum field strength of the magnetic separator.

* * * * *